(12) United States Patent
Coopersmith

(10) Patent No.: US 7,153,134 B2
(45) Date of Patent: *Dec. 26, 2006

(54) GINGIVAL RETRACTION DEVICE AND METHOD

(76) Inventor: Allan Coopersmith, 5757 Decelles Avenue-Suite 520, Montreal (CA) H3S 2C3

( * ) Notice: Subject to any disclaimer, the term of this patent is extended or adjusted under 35 U.S.C. 154(b) by 0 days.

This patent is subject to a terminal disclaimer.

(21) Appl. No.: 11/020,207

(22) Filed: Dec. 27, 2004

(65) Prior Publication Data

US 2005/0118552 A1   Jun. 2, 2005

Related U.S. Application Data

(63) Continuation-in-part of application No. 10/734,233, filed on Dec. 15, 2003, now Pat. No. 7,033,173, which is a continuation of application No. PCT/CA02/00910, filed on Jun. 17, 2002.

(60) Provisional application No. 60/532,805, filed on Dec. 29, 2003, provisional application No. 60/302,030, filed on Jul. 2, 2001, provisional application No. 60/298,201, filed on Jun. 15, 2001.

(51) Int. Cl.
*A61C 9/00* (2006.01)

(52) U.S. Cl. ...................... 433/136; 433/215

(58) Field of Classification Search ............... 433/136, 433/215, 40, 141, 138, 139
See application file for complete search history.

(56) References Cited

U.S. PATENT DOCUMENTS

| 3,151,393 | A | 10/1964 | Holmes |
| 3,238,620 | A | 3/1966 | Robertson |
| 3,541,689 | A | 11/1970 | Wilford |
| 4,396,375 | A | 8/1983 | Gores |
| 4,465,462 | A * | 8/1984 | Ticknor ............ 433/136 |
| 4,617,950 | A | 10/1986 | Porteous et al. |
| 4,677,139 | A | 6/1987 | Feinmann et al. |
| 4,871,311 | A * | 10/1989 | Hagne ............. 433/136 |
| 4,892,482 | A | 1/1990 | Lococo |
| 4,930,920 | A | 6/1990 | Fitzig |
| 5,022,859 | A * | 6/1991 | Oliva ............... 433/141 |
| 5,213,498 | A | 5/1993 | Pelerin |
| 5,358,403 | A * | 10/1994 | Groth ............... 433/136 |
| 5,362,495 | A | 11/1994 | Lesage |
| 5,480,303 | A | 1/1996 | Groth |
| 5,676,543 | A | 10/1997 | Dragan |
| 6,116,905 | A | 9/2000 | Hoos |
| 6,170,714 | B1 | 1/2001 | Lesage |
| 7,033,173 | B1 * | 4/2006 | Coopersmith ....... 433/136 |

FOREIGN PATENT DOCUMENTS

| CA | 2441907 | 12/2003 |
| DE | 3122834 A | 12/1982 |
| DE | 9211339 U1 | 11/1992 |
| DE | 29912502 U1 | 2/2000 |
| FR | 2761591 A1 | 10/1998 |

OTHER PUBLICATIONS

International Search Report Dated Sep. 23, 2002 in PCT/CA02/00910.

* cited by examiner

*Primary Examiner*—Ralph A. Lewis

(57) ABSTRACT

A device for retracting gingival tissue away from a tooth or plurality of teeth prepared to receive a dental prosthesis comprising a retraction material associated with a provisional restoration to be packed into a sulcus associated with the prepared tooth. The device is preferably compressible, deformably rigid, extensile and non-elastic and will not stick to the gingiva or tooth structure thereby allowing for atraumatic removal leaving a dry open sulcus. A method of use is also disclosed.

9 Claims, 9 Drawing Sheets

GINGIVAL RETRACTION DEVICE AND METHOD

The present application is a continuation-in-part of U.S. patent application Ser. No. 10/734,233, entitled "Gingival Retraction Device and Method" filed Dec. 15, 2003 now U.S. Pat. No. 7,033,173. Through the '233 application, the present application is a continuation of International Patent Application serial No. PCT/CA02/00910 entitled "Gingival Retraction Device and Method" filed Jun. 17, 2002 and designating the United States of America. Through the '233 and '00910 applications, the present application claims the benefit of U.S. Provisional Patent Applications Ser. No. 60/298,201 entitled "Gingival Retraction Device and Method" filed Jun. 15, 2001 and Ser. No. 60/302,030 entitled "Retractowedge Gingival Retraction Device" filed Jul. 2, 2001. The present application also claims the benefit of U.S. Provisional Patent Application Ser. No. 60/532,805 entitled "Gingival Retraction Device and Method" filed Dec. 29, 2003. The contents of all of the aforementioned applications are incorporated herein by reference.

FIELD OF THE INVENTION

This invention relates to apparati and methods employed by dental practitioners to retract gingival tissues from around the base of a tooth, or a plurality of teeth, to control oral bleeding and provide gingival tissue fluid control, such as for a tooth or teeth which has been prepared by drilling or other means to receive a dental restoration, such as a crown, inlay, onlay or implant supported prosthesis.

BACKGROUND OF THE INVENTION

Around each healthy tooth in the mouth of a human is a narrow groove termed a sulcus, which separates the tooth from the surrounding gingival tissue at the surface of the tissue. Certain dental procedures, such as those to create an impression of the tooth and those to create a prosthetic for the tooth, require that the gingival tissue be retracted from the tooth in the area of the sulcus. While the prior art teaches several means of accomplishing this retraction, none is optimal.

One commonly employed conventional method is through the use of retraction cord. Simply described, retraction cord is length of cord that is wrapped around the base of the tooth several times and then manually forced into the sulcus by a dental practitioner. The manual force will cause the gingival tissue to separate from the tooth and the presence of the cord will prevent the tissue from returning to its original state. Unfortunately, the use of retraction cord has several drawbacks. First, the cord is typically supplied by manufacturers wound on a spool, packed into a container. To use the cord, the dental practitioner must estimate the amount required for the particular application. Since the cord must be wrapped around to tooth while the ends are held in one hand by the practitioner, a significant amount of cord is wasted in the process. Second, it is very difficult to force and maintain the cord within the entire sulcus (around the entire circumference of the tooth) at the same time. It is very common for the force required to insert the cord into one area of the sulcus to cause cord already inserted to other areas of the sulcus to exit the sulcus. This requires the practitioner to repack those areas causing tearing and abrasion of the inner lining of the sulcus, leading to bleeding and/or exuding of crevicular fluid, which may cause contamination and/or inaccuracies in the dental procedures to be performed. Third, inherent in the process is that the cord does not conform well to the various depths and widths of the sulcus nor the irregularities of any prepared tooth margins. Finally, the entire process is relatively time consuming. Removal of said cord with a dental instrument is a delicate procedure often leading to trauma and bleeding of gingival tissue.

Another type of retraction cord is made of strands of a fiber such as cotton stiffened with a stiffener strand such as for example a copper wire threaded through the core of the cord. The stiffener is made of material that provides the cord with deformability. Positioning of this type of the cord over the whole periphery of the tooth is delicate. In addition, because of the stiffener strand, this process is relatively painful and generally requires a local anesthesia. Moreover as one end of this stiffened strand is packed into the sulcus, the other end tends to become displaced out of the sulcus. A frequent lesion is observed of the epithelial attachment as well as hemorrhages or oozing upon withdrawal of the cord. In addition, this type of cord suffers from some of the other above-noted drawbacks associated with retraction cords.

A second commonly employed method is through the use of an injectable paste. In this method a relatively large needle is placed in the sulcus and is used to inject a biocompatible paste therein under relatively high pressures (between 13,000 and 30,000 Pascals). This method too has several disadvantages. Typically, either the needle itself or the paste injected under high pressure or both cause trauma to the gingival tissue. Moreover, the paste is stiff and does not adhere well to moist tissues and typically is displaced out of the sulcus. This paste must often be packed down into the sulcus with a piece of cotton or a dental instrument. Because of the high pressures involved, the paste injection device (commonly termed a "gun") is complicated, expensive and suffers frequent breakdowns (as does the actual paste container). Furthermore the paste must be washed off with a water spray and then dried with compressed air before the impression can be taken. This is an additional step and this water and then air spray will often lead to bleeding within the sulcus.

A third method is the use of a ring of material or a metal collar which is placed into the sulcus with an instrument and which is used to retract the gingiva away from the tooth. These rings have the same problem as the strands and cords in that an instrument is needed to pack the ring into the sulcus causing discomfort, bleeding. They must be retrieved and or removed with a dental instrument prior to the taking of an impression, which also causes discomfort, bleeding and trauma.

A third conventional method is the use of a pressure cap. A pressure cap is a cap made of a spongy material that is fitted around the tooth and causes retraction of the gingival tissue through the application of pressure. The difficulty here is that the shape of the cap is even and constant while that of the sulcus (depth and width) is not. Therefore this method is imprecise and does not ensure accurate nor sufficient retraction. For these reasons, it is presently only used to ensure haemostatis after a procedure of gingival eviction (described below).

An additional convention method is termed gingival eviction. In this method the gingival tissue is retracted by electric bistoury, laser, or by a diamond charged drill ("diamond curretage"). None of these procedures, however, is not without its drawbacks. Electric bistoury and laser generally mutilate the gingival tissue and are therefore quite painful and require local anesthesia. Similarly diamond curretage is also quite painful and causes prolific bleeding. Each of these procedures is traumatic and creates gingival shrinkage and recessions leading to undesirable unprotected root coverage.

There is therefore a need in the art for an improved apparatus for, and method of, retracting gingival tissue from a tooth, which are preferably more efficient and less traumatic than conventional methods.

SUMMARY OF THE INVENTION

It is therefore an object of an aspect the present invention to provide an improved apparatus for retracting gingival tissue from a tooth.

It is a further object of an aspect of the present invention to provide an improved method for retracting gingival tissue from a tooth.

In one aspect, as embodied and broadly described herein, the present invention provides a device for retracting gingival tissue away from at least one tooth, the device comprising a retraction material to be packed into a sulcus associated with the at least one tooth, the material being associated with the provisional restoration i.e."temp" and then placed onto the prepared tooth stump, i.e. "abutment". Pressure is exerted onto the temp by finger pressure or by having the patient bite down on a cotton roll or other object, which is placed on the biting surface, "top" of the temp. This causes the thick gel or paste-like material to be expressed into the sulcus and beyond the prepared tooth margin thereby retracting, widening and displacing the gingival away from the tooth margin. Because the "temp" conforms intimately to the prepared tooth margin, the (hydrolic) pressure exerted by the compressed "temp" distributes the retraction material precisely and equally beyond the prepared tooth margin. Similarly, the provisional restoration, "temp" which is compressed over most retraction materials and devices will improve and increase the efficiency, and effectiveness of these retraction devices.

One can use an impression of the abutment tooth taken preliminary to retraction and the final impression in a way similar to using the "temp" to compress the retraction material into the sulcus; it should be understood that references to the "temp" should also include and describe procedures if the preliminary abutment tooth impression using impression material, or thermoplastic material or other rigidly deformable material was used instead of the "temp".

A tooth may be prepared for dental procedure via conventional methods to create a tooth abutment having a tooth margin. The margin may be described as a small shelf like area extending from the tooth abutment to the edge of the tooth in the area of the gumline. Generally, the tooth is prepared such that the sulcus is located axially outward from the tooth margin. In order to perform further dental procedures on the tooth, the sulcus must be enlarged such that the gingival tissue is further away from the tooth margin.

The retraction material of the present invention is used for this purpose. The retraction material is associated with the "temp" and the temp holding the retraction material is then compressed over the prepared tooth abutment, allowing the retraction material to be placed over the tooth in the area of the margin and to be packed (forced) into the sulcus distributing evenly and conforming to the prepared tooth margin. This compression causes axial and apical pressure on the gingival tissue causing it to retract away from the tooth margin. Moreover this pressure is even and steady and precise around the margin of the prepared tooth. Additional gingival retraction can be achieved by packing the extruded retraction material back into the sulcus using a dental instrument.

The retraction material may be associated with the "temp", as for instance, as a non limiting example, as being placed into the interior of the cavity of the "temp" corresponding to the negative form of the prepared tooth abutment. The retraction material may be associated with the "temp" also as for instance as a non limiting example as being placed on the interior and edge of the margin of the "temp" or may first be placed into the sulcus.

Unlike other retraction methods which require constant monitoring by the dentist or assistant to control the ejection of retraction material from the sulcus by the cheek or tongue or saliva, the patient can be left alone during this retraction period. This allows the dentist and assistant to direct their time and attention elsewhere. The patient is stable and biting on a cotton roll throughout the retraction process.

The present invention overcomes the deficiencies of the prior art in several respects. The temp serves a template and/or vehicle to insert the retraction material into the sulcus in a quick and efficient manner. It compresses the retraction material quickly, evenly and precisely and efficiently well beyond the prepared tooth margin, and this retraction material is held solidly in the sulcus by the temp during the entire retraction period. This is an improvement over other retraction methods which require pressing cords and rings with small dental instruments into the sulcus which is time consuming, tedious, inefficient and traumatic often causing bleeding and ejection of the cord from the sulcus on one side as the other side is pressed down. The tongue and cheek and saliva, suction tubes, often dislodge or wash away cords or pastes not protected by a temp. Thus, packing of the sulcus in the same area several times, and the tearing and/or abrasions associated therewith are minimized or avoided. Mutilation of the gingival tissue is avoided. The retraction material does not adhere to the gingiva or tooth and therefore eliminates the need to wash and dry the sulcus prior to impression taking. Therefore, this additional step, which can lead to bleeding or oozing from the sulcus, is eliminated. The Retraction material releasably adheres to the "temp" so that when the "temp" is withdrawn, so is the retraction material allowing for simple and atraumatic removal of the retraction device leaving a dry open sulcus ready to receive the impression material. The retraction material can then be removed easily from the internal cavity of the "temp" following the impression and the "temp can then be cemented over the prepared abutment with temporary cement. As the "temp" is usually made as part of the prosthesis fabrication, no additional steps or materials are necessary thereby saving time and money.

Moreover, retraction material of the present invention is easy to handle and to place, is inexpensive, precise and efficient and can be used for single or multiple restorations. It does not adhere to the gingiva nor tooth abutment. It is held in place securely by the "temp" preventing displacement by the patient's tongue, cheek, saliva, dental instrument etc. The "temp" also holds the retraction material or most other retraction materials securely and as well, allows for additional retraction to be achieved by compressing most of these retraction devices back into the sulcus with a plastic instrument. The compression of the retraction material also aids in hemostasis.

Finally, the retraction material of the present invention allows for faster, more accurate and less damaging gingival retractions, leading to better results from the dental procedures (e.g. preparing a crown) that they are intended to facilitate.

The retraction material of the present invention is a semi solid or a gel or silicone or putty type of material or a material or a paste which transforms or hardens or sets into a semi solid or gel and is of a consistency that it attaches to the temp and can be withdrawn from the sulcus atraumatically and withdraws easily as the provisional or temporary is withdrawn from the prepared tooth abutment. (rather than remove each strand of retraction cord individually (multiple cords for multiple teeth), or wash off unset paste, i.e Expasyl with vigorous spray which many times promotes bleeding.

Expasyl adheres to the gingiva and tooth abutment. Preferably, the retraction material will not adhere to the gingiva nor tooth abutment. As the set retraction material is removed from around prepared tooth it leaves a dry open sulcus ready for impression material (doesn't have to be washed and dried.)

As used in the context of the present specification, the term retraction material is intended to include any material whether solid, semisolid or liquid which is as a non-limiting examples in the form of a putty, gel, gelatin, paste, silicone, polyvinylsiloxane, polyether. The retraction material may harden or set. The hardening or setting of the retraction material may occur chemically or by the elapse of time and thereby allows for increased compression of the sulcus, and/or manipulation or re-packing of the partially hardened, or hardened retraction material back into the sulcus with a dental instrument. The hardening or setting of the material also aids in the removal of same from the sulcus in an atraumatic manner.

The retraction material can be used to retract tissues around a singular prepared tooth abutment or a plurality of tooth abutments. It should be understood that since each human has several different types of teeth, each being of different size, and that since the size of the same type of tooth will vary between humans, the retraction paste fills the interior of the provisional restoration which has been accurately and custom fit to the tooth or teeth abutments and therefore will be of the ideal size, amount, accuracy, precision to retract the sulcular tissues adjacent to the gingival margin or margins. It should also be noted that if a the retraction material is made to harden or set, then the retraction material can be made to harden or set at variable speeds and consistencies to retract the sulcus around a variety and number of tooth or teeth abutments. For example the retraction material can be made to harden or set more slowly to allow for more time (working time) to fill and place the temp over a plurality of teeth.

It is highly preferable that the retraction material be compressible. The consistency of the retraction matreial should be able to be placed into the interior of the provisional restoration, "temp", and not run out when the temp is inverted and then placed on the tooth abutment. Deformability is highly desirable as the retraction material must flow along the top and axial contours of the tooth abutment and then down into the sulcus. As part of its deformability the retraction material may need to be extensile to accommodate being placed back into the sulcus with a dental instrument. The retraction material can be expansile. The retraction material should be resistant to tearing while being deformed. Once deformed it should retain its new shape. It should not tend to return to its original pre-deformation shape because this impedes gingival tissue retraction.

Further, it is highly preferable that the retraction material be deformably rigid. In order that the retraction material be easy to work with during its insertion into the temp and then into the sulcus, the retraction material should partially retain its shape (not deform) under forces less than the amount necessary to compress it into the sulcus. In this manner, the retraction material will be able to be removed easily from the prepared tooth abutment and the patient's mouth.

The material(s) of which the retraction material is constructed preferably is (are) one (or more) selected from the group consisting of sponge, gel, jelly, foam, putty, cellulose, polyvinylsiloxane, polyeteher, silicone, plastic, powder/liquid mixture, or paste. Preferably, the material is a mixture of 1.25 grams Coe Comfort powder, 0.2 grams of Zinc Oxide, mixed with 0.75 mls. Coe Comfort liquid and 0.25 mls. Hemodent. More preferably the retraction material can be a mixture of equal quantities of regular set or fast set impression material putty base and catalyst which may contain any combination of, but not limited to, fillers, fibers, modifiers.

Where the retraction material comprises more than one material, it may comprise either a homogenous mixture of materials or separate and distinct layers of different materials or mixtures of homogenous materials. In such cases is it preferred that the retraction material comprise a thin layer of a fluid-impervious material (e.g. akin to the barrier layer of a conventional sanitary napkin), and a layer of retraction material of a sponge, gel, jelly, foam, putty, cellulose, polyvinylsiloxane, silicone, plastic, paste. (e.g. the described hereinabove). The previous described web of material may comprise several different types of layers. By way of non-limiting example, the layers may be a fibrous layer, a paste layer, and gelatinous layer.

It should be understood that the retraction material may contain or be dipped or soaked or otherwise impregnated with or otherwise contain or carry other medical ingredients without departing from the scope of the present invention. By way of non-limiting example, such ingredients may be astringents, antiseptics, antibiotics, and hemostyptics.

The retraction material of the present invention may be manufactured by any conventional means appropriate for the materials of which they are constructed. As a non-limiting example, the retraction material may be formed by mixing a powder and a liquid or a paste and a paste, or a paste and a liquid or a paste and a powder, or a gel with one or more of the aforementioned. The constituents may be mixed either by hand or in a mixing device such as but not limited to an automixing chamber ("automixing gun" or "automixing syringe") or in a capsule which is then triturated or mixed in a dental triturator. By way of non-limiting example the components may be contained in separate compartments of a dental capsule and then activated (the internal membrane is punctured allowing the components to be mixed) and then triturated in a dental triturator. This capsule can have a nozzle through which the mixed retraction material can be inserted into the interior of the temp. The retraction material may be made of one or a combination of materials which do not require mixing but have some or all of the necessary properties as aforementioned. The retraction material may harden or set simply by being exposed to air and/or moisture.

Whatever the composition of the material, it is preferred that the material be compressible in use. The material should be able to be compacted while the retraction material is being compressed and packed into the sulcus, and in this manner, the material will be under pressure once forced therein. The pressure caused by the compressed state of the material will aid in forcing the sulcus to expand and retracting the gingival tissue. An additional benefit of the compression of the retraction material on the sulcular tissue is to produce hemostasis. It may also be desirable that the material be somewhat absorbent so that fluids being exudated from the body into the sulcus are contained and maintained away from the tooth where they could negatively interfere with the dental procedures to be performed. Further absorbent materials generally tend to increase in size as they absorb, thus in the present case, increasing the amount of pressure on the gingival tissue and thereby the retraction and hemostasis. It is a preferred embodiment of the present invention that the retraction material may be deformable, extensile.

The retraction material which is held in place securely by the "temp" thereby preventing displacement by any or any combination of the patient's tongue, cheek, saliva, dental instrument; the "temp." allows for additional retraction to be achieved by compressing the retraction material as well as most other existing retraction devices back into the sulcus with a plastic instrument and in so doing compresses the retraction material into the sulcus producing additional retraction where needed. The retraction material of the present invention which is a semi solid or a gel, or putty or silicone type of material or a material or a paste which can transform or harden or set into a semi solid. This retraction material can be of a consistency that allows it to attach to the "temp." and can be withdrawn from sulcus atraumatically and withdraws easily as the provisional or temporary is withdrawn from the prepared tooth abutment.

The retraction material may harden or set. The hardening or setting of the retraction material may occur chemically or by the elapse of time or by light activation.

The retraction material may be resistant to tearing while being deformed. Once deformed it should retain its new shape. It should not tend to return to its original pre-deformation shape because this impedes gingival tissue retraction. The retraction material may preferably be deformably rigid; the retraction material should partially retain its shape (not deform) under forces less than the amount necessary to compress it into the sulcus.

The retraction material preferably may be constructed preferably from one (or more) selected from the group consisting of sponge, gel, jelly, foam, putty, cellulose, polyvinylsiloxane, polyether, silicone, plastic, powder/liquid mixture, or paste.

Preferably, the material is a mixture of 1.25 grams Coe Comfort (trademark) powder, 0.2 grams of Zinc Oxide, mixed with 0.75 mls. Coe-Comfort (trademark) Edentulous tissue conditioner liquid and 0.25 mls. Hemodent (Aluminum chloride-6-hydrate 21.3% aqueous solution or powder). The proportions of this mixture may be modified to change preferred working time and consistency.

More preferably the retraction material can be a mixture of regular set or fast set impression material putty base and catalyst which may contain any combination of, but not limited to, fillers, fibers, modifiers.

Where the retraction material comprises more than one material, said retraction material may comprise either a homogenous mixture of materials or separate and distinct layers of different materials or mixtures of homogenous materials. By way of non-limiting example, the layers may be a fibrous layer, a paste layer, gelatinous layer and a putty layer.

The retraction material may contain or be dipped or soaked or otherwise impregnated with or otherwise contain or carry other medical ingredients without departing from the scope of the present invention. By way of non-limiting example, such ingredients may be astringents, antiseptics, antibiotics, and hemostyptics.

The retraction material of the present invention may be manufactured by any conventional means appropriate for the materials of which they are constructed. As a non-limiting example, the retraction material may be formed by mixing a powder and a liquid or a paste and a paste, or a paste and a liquid or a paste and a powder, or a putty and a putty, or a gel with one or more of the aforementioned, or any combination therof.

The retraction material may be made of one or a combination of materials which do not require mixing but have some or all of the necessary properties as aforementioned. The retraction material may harden or set simply by being exposed to air and/or moisture. The retraction material may be deformably rigid and may compress the gingival tissue without setting.

The retraction material may be somewhat absorbent.

In addition, it is highly preferred that the material be atraumatically removable from the suclus. Ideally, the material should not have any component that bonds to either the ginvigal tissue or the tooth making removal of the retraction material difficult or causing damage to either. Ideally, the retraction material should be able to be removed from the sulcus as simply as it was inserted via being pulled out by withdrawing the temp (the retraction material slightly adhering to the temp) with a forcep type of dental instrument.

In another aspect, as embodied and broadly described herein, the present invention provides a method of preparing a tooth for a dental procedure comprising the steps of: removing a portion of a tooth to create a tooth abutment; placing retraction material as described hereinabove into the cavity of the provisional prosthesis i.e. "temp"; and packing the retraction material into a sulcus associated with the tooth. Unless it is biodegradable or soluble, the retraction material should be removed simply and atraumatically from the sulcus at the appropriate point in the procedure. Following the retraction and impression stages the retraction material can be easily and quickly withdrawn from the interior cavity of the "temp" with a dental explorer or other dental instrument.

In a preferred embodiment, once the tooth has been prepared to create a tooth abutment, a provisional restoration is prepared (both by conventional methods). As opposed to the dental practitioner simply manually packing a cord or loop into the sulcus, once the retraction material has been placed into the cavity of the provisional restoration, the provisional restoration is placed on top of the prepared abutment. The patient is instructed to bite down on the provisional restoration. The occlusal pressure thus exerted will cause the retraction material to be forced into the sulcus all around the tooth nearly simultaneously and to conform to the irregularities of the prepared tooth margin. Should the patient have no tooth opposing the provisional restoration a relatively large cotton wad may be placed thereon (enabling the patient to bite down) or alternatively, the dental practitioner may apply manual pressure.

In a most preferred embodiment, the retraction material can simply be placed into the cavity of the "temp" with a spatula or dental instrument or automixing gun or syringe. Or, the retraction material can be injected into the sulcus with a simple syringe i.e. CR syringe or auto syringe and then the temp can be placed over the retraction material thereby compressing it into the sulcus.

In a preferred embodiment, the retraction material can simply be placed onto the edge and internal aspect of the edge of the "temp" with a spatula or dental instrument or automixing gun or syringe and then the temp can be placed over the abutment, thereby compressing the retraction material into the sulcus.

In a most preferred embodiment, again, once the tooth has been prepared to create a tooth abutment, a provisional restoration is prepared. The retraction material is then releasably adhered to the gingival margin, but slightly adhesive to the provisional restoration (having the retraction material adhered thereto) and is placed on the tooth and the patient is instructed to bite down on the provisional restoration. The occlusal pressure thus exerted will cause the retraction material to be forced into the sulcus all around the tooth nearly simultaneously.

In any of the above methods, before the patient bits down, optionally, a piece of cotton or other similar fiber may be placed on top of the provisional restoration, to aid in the process. Further, it is also possible for the dental practitioner to manually pack the retraction material into the sulcus after one of the non-manual packing methods described above have been employed, should additional packing be desired or required. Finally, there is an additional benefit in that in many situations a portion of the retraction material will remain trapped between the provisional restoration and the tooth margin (while the majority is packed into the sulcus). The retraction material being trapped by the "temp" aids in anchoring the retraction material in place and preventing it from exiting the sulcus, either by the patient (by accident) or the dental practitioner (during additional manual packing of the loop, for example).

A pressure cap which may be composed of but not limited to either or any combination of cotton, polyvinylsiloxane, polyether, polypropylene, polyethylene, or paper, can be used in a manner similar to the "temp." or provisional restoration.

In the above paragraphs, the present invention has been described in terms of a single tooth. It is, however, within the scope of the present invention that a retraction device be constructed for use with more than one tooth. Thus, as embodied and broadly described here, the present provides a device for retracting gingival tissue away from a plurality of teeth, the device comprising a retraction material to be packed into a sulci associated with the plurality of teeth. As a non-limiting example the retraction material can have a longer working time or setting or hardening time to allow additional time to fill the cavities of a plurality of teeth, to place the temp or temps on the abutments, and compress the temps in a gingival direction extruding the retraction material into the sulcus.

In this aspect the retraction material described hereinabove is inserted into the abutment cavities of the provisional restoration made to temporize the plurality of prepared teeth. This structure may be used when more than one tooth is being prepared for a dental procedure. The dental practitioner simply inserts the retraction material into each of the temporary tooth abutment cavities and places the temp over the abutment teeth thereby compressing the retraction material into the sulci of the plurality of prepared teeth. Removal of the device is simply the reverse of this process.

It is important to note that it takes only a few seconds longer to retract the gingiva around a plurality of teeth (up to 16 teeth) using this method as it takes for one tooth thereby saving significant time and expense.

Other objects and features will become apparent by reference to the following description and the drawings.

DESCRIPTION OF THE DRAWINGS

A detailed description of preferred embodiments of the claimed invention is provided hereinbelow, with reference to the following drawings, in which:

FIG. 12 is a longitudinal cross section view of an embodiment of a device of the present invention suitable for use with a plurality of teeth illustrating the effective, continuous, retraction of the sulcii of the plurality of teeth on the facial and lingual as well as interproximal aspects.

Figure 1:
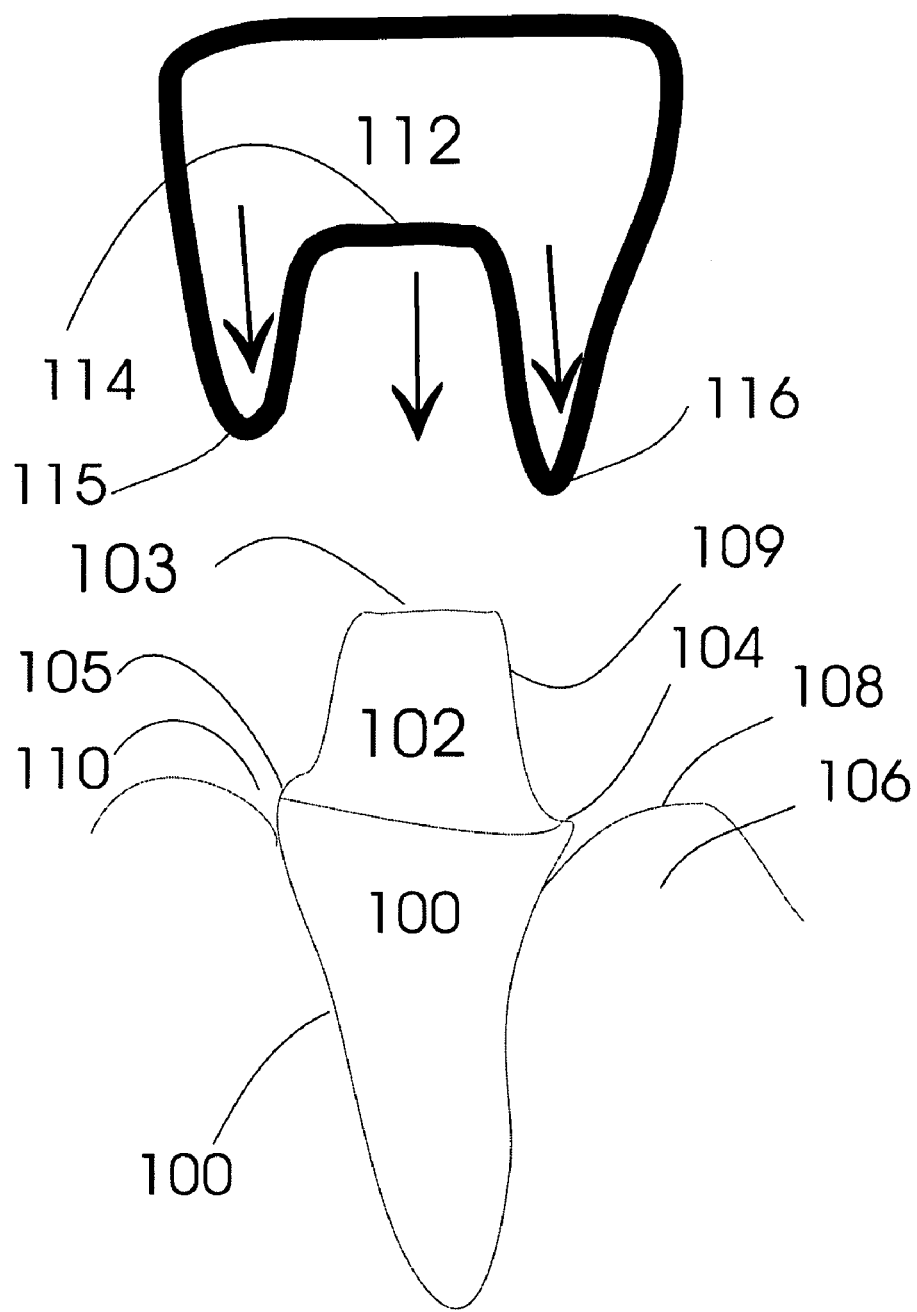
FIG. 1 is a longitudinal cross-sectional view of a human tooth and a provisional restoration.

In the drawings, preferred embodiments of the invention are illustrated by way of example. It is to be expressly understood that the description and drawings are only for purposes of illustration and as an aid to understanding, and are not intended to be a definition of the limits of the invention.

DETAILED DESCRIPTION OF PREFERRED EMBODIMENTS

Referring to FIG. 1 there is illustrated a human tooth 100 that has been prepared for a dental procedure by conventional means. Specifically the surface tooth structure of the tooth 100 has been removed creating a tooth abutment 102 having a tooth margin 104, 105. The tooth 100 is embedded in gingival tissue 106 having a gingival crest 108. Between the gingival tissue 106 and the tooth 100 is located a sulcus 110.

A provisional restoration 112 has been fabricated by conventional means from a dental impression to register with the prepared tooth 102. The provisional restoration, "temp", 112 has an interior surface 114 and a distal temp margin 116, and a mesial temp margin 115 that are together configured to conform to the tooth abutment 102 and the mesial tooth margin 105 and the distal tooth margin 104. As can be seen in the drawings the preparation of the tooth 100 and thus the provisional restoration 112 may not be symmetric about the center of the tooth 100.

Figure 2:
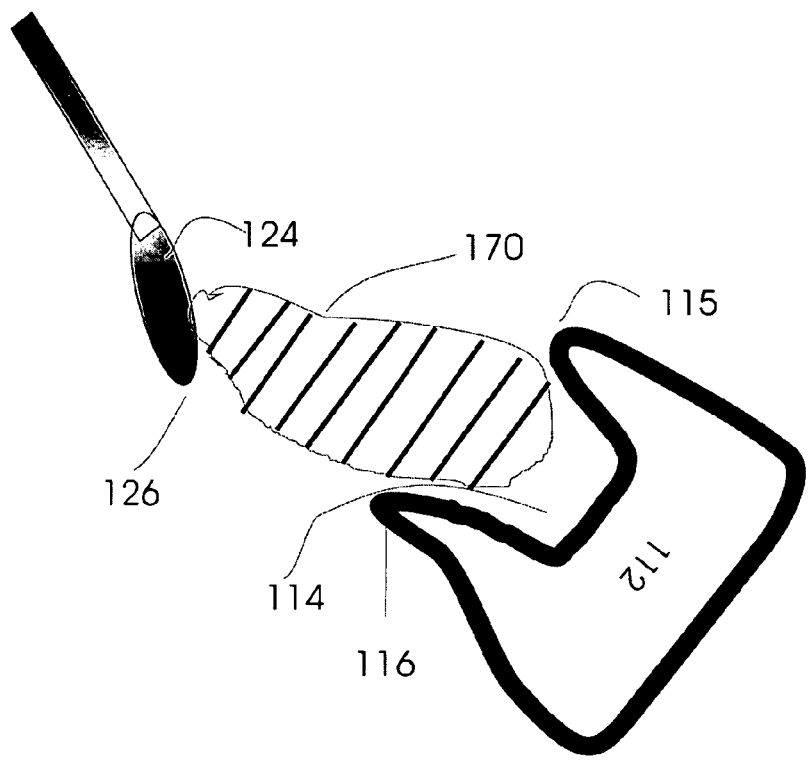
FIG. 2 is a longitudinal cross-sectional view of an embodiment of the retraction material of the present invention as it is being loaded into the cavity of the provisional restoration.
Figure 2:
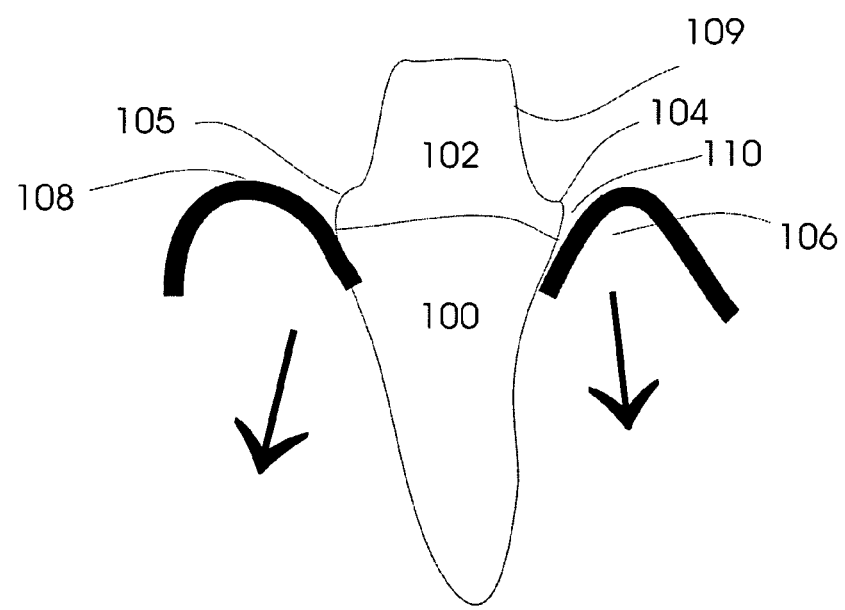

Referring to FIG. 2, there is shown a first embodiment of the retraction material 170 of the present invention. The retraction material 170 is placed into the cavity of the "temp" against the interior surface, 114 with the blade 124, of the dental instrument 124.

Figure 5:
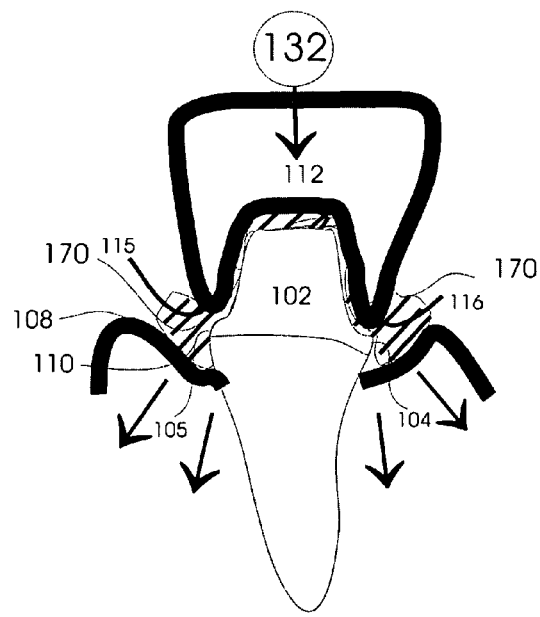
FIG. 5 is a longitudinal cross-sectional view of a human tooth as in FIG. 1 illustrating the packing of a first embodiment of a device of the present invention into a sulcus via the compression of the retraction material by the provisional restoration.

Care is taken to overfill the cavity of the "temp" to ensure proper retraction. The overflow will gently and atraumatically deflect and spill out of the sulcus as seen in FIG. 5. The retraction material can be inserted by way of a syringe type apparatus (not shown) as for instance but not limited to an automix syringe.

Figure 3:
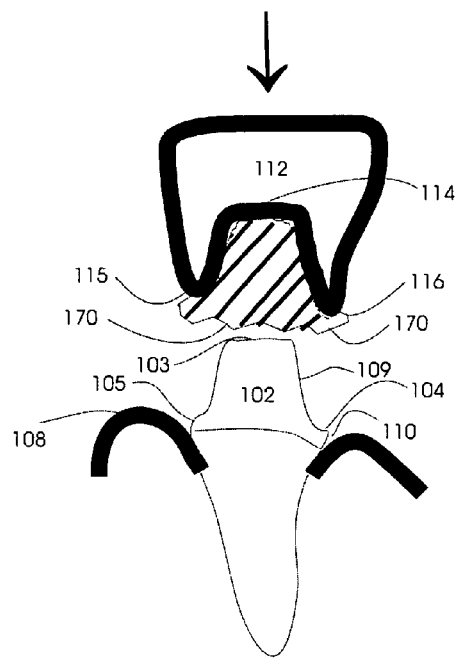
FIG. 3 is a a longitudinal cross-section of the embodiment shown in FIG. 2 as it is being inserted onto the prepared tooth abutment.
Figure 4:
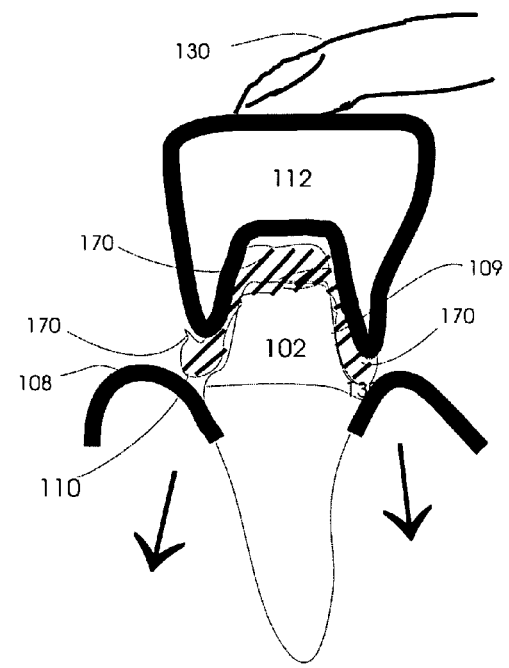
FIG. 4 is a longitudinal cross-sectional view of a human tooth as in FIG. 1 illustrating the compression and flow of an embodiment of a device of the present invention along the axial surface of the prepared tooth abutment in an apical or gingival direction.

Referring to FIGS. 3, 4, retraction material 170, contained in the "temp" 112 has been placed over the tooth abutment 102 with thumb or forefinger 130 or a dental clamp or forceps (not shown). Attention is taken to place the "temp" 112 over the middle of the abutment 102 so that the retraction material will be compressed equally.

Referring to FIG. 4. Finger pressure 130 is exerted to compress the retraction material over the tooth abutment 102 along its axial walls 109. The retraction material 170 is compressed and extruded along the axial walls 109 of the abutment 102 moving in an apical direction towards the sulcus 110.

Figure 6:
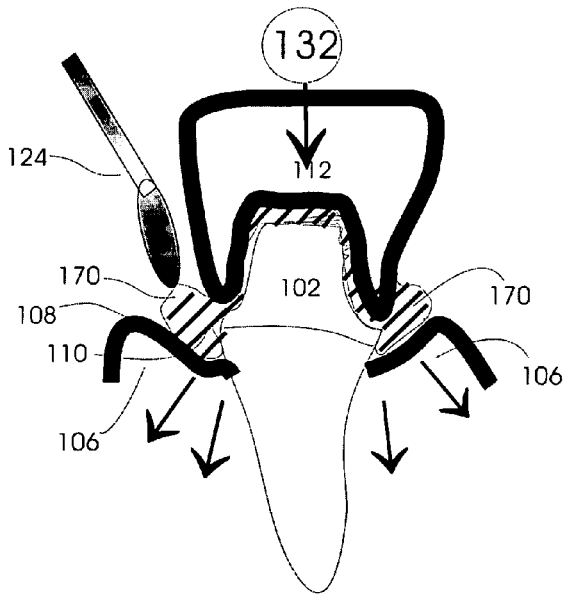
FIG. 6 is a longitudinal cross-sectional view similar to FIG. 6 illustrating the additional retraction achieved by packing the extruded retraction material back into the sulcus with a dental instrument.
Figure 8:
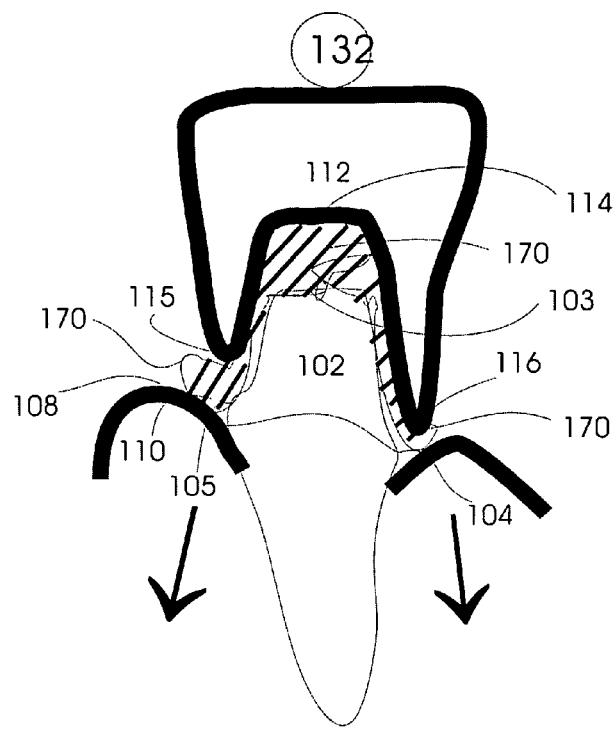
FIG. 8 is a longitudinal cross-sectional view similar to FIG. 4 illustrating the compression and flow of the first embodiment of the retraction device as it extrudes precisely to adapt to the uneven and more apically located gingival margin of the provisional restoration.
Figure 9:
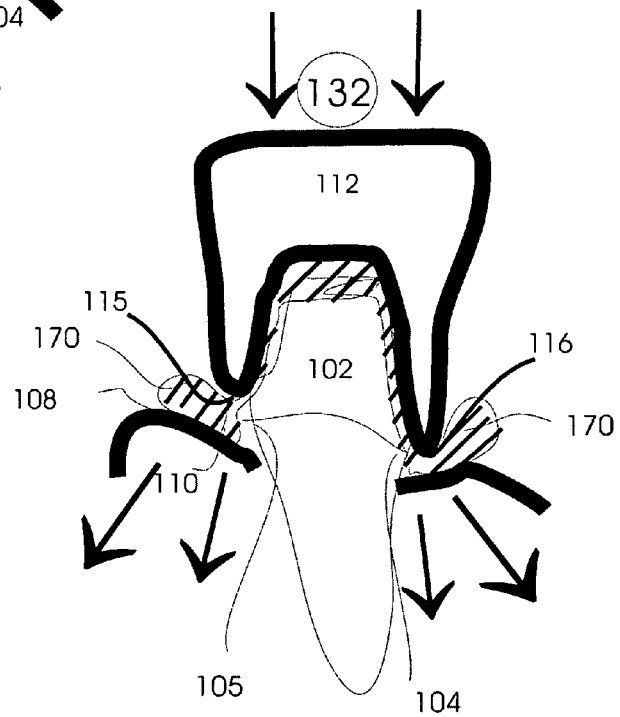
FIG. 9 is a longitudinal cross-sectional view similar to FIG. 9; demonstrating how the margins of the provisional restoration precisely guides the extrusion of retraction material into the sulcus thereby producing precise and even and confluent retraction.

Referring to FIG. 5. The patient is then asked to bite down on the provisional restoration 112, and as shown in FIGS. 5, 8, and 9. the occlusal force exerted by the patient causes the retraction material 170 to be forced into the sulcus 110 nearly simultaneously and precisely around the entire circumference of tooth 100. In doing so, it is possible (as is shown in FIGS. 5 and 6) that a portion of the retraction material 170 will remain trapped between the provisional restoration margin 116 and the tooth margin 104. This trapped portion 170 serves to anchor the retraction material 170 and prevent it from being displaced from the sulcus 110. A piece of cotton 132 may be optionally placed on the tooth 100 before the patient is instructed to bite down. The overflow will gently and atraumatically deflect and spill out of the sulcus.

As shown in FIG. 6, if the retraction of gingival tissue 106 is insufficient after the provisional restoration 112 has caused the retraction material 170 to be packed in the sulcus 110, or if for some reason a portion of the retraction material otherwise interfere with the dental procedure, the practitioner may cause additional packing through the application of manual force on retraction material via a dental instrument 124. This will cause more of the retraction material 170 to be packed in the sulcus 110 providing additional retraction. A significant advantage of using the "temp." to hold down the retraction material without being dislodged as the retraction material is being compressed into the sulcus is clearly demonstrated.

Figure 7:
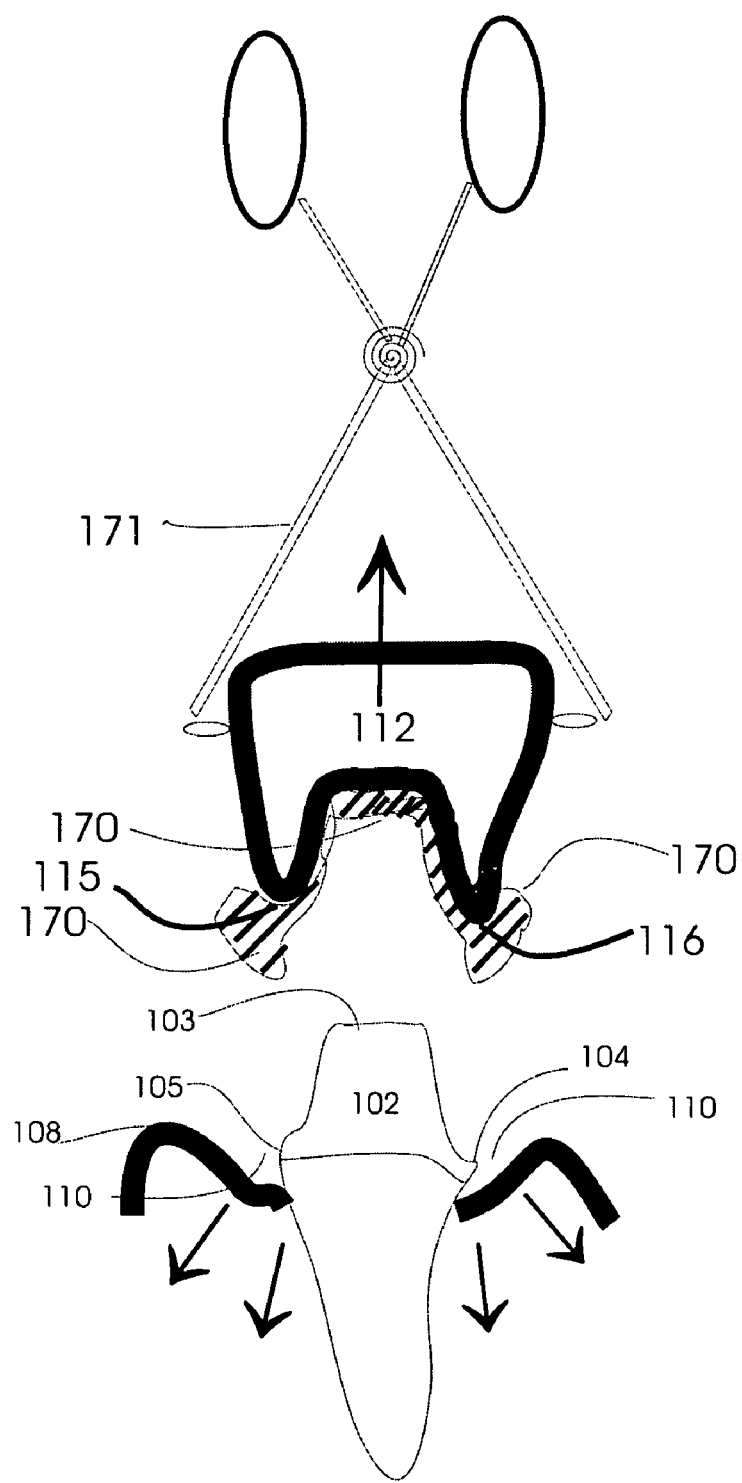
FIG. 7 is a longitudinal cross-sectional view illustrating the atraumatic removal of the retraction material as it is attached to and coincidentally withdrawn with the provisional restoration by dental forceps.

FIG. 7. Illustrates the atraumatic removal of the set or hardened retraction material 170 from around the tooth abutment 102, while it sticks to the interior of the "temp" 112, as the temp is removed with dental forceps 171 leaving the sulcus 110 open and dry. The set or hardened retraction material takes on the outline of the tooth abutment 102, and the root below or apical to the abutment margin 104, 105.

FIG. 8 illustrates how the retraction material 170 is directed towards the margins of the prepared abutment 102 by the "temp" 112. The unevenness and assymetry of the abutment margin is seen as the mesial abutment margin 105 is located more occlusally (higher) than the distal abutment margin 104 which is located more apically (lower). Because the temp was fabricated to fit precisely the abutment margin of the prepared tooth, the distal margin of the temp 116 corresponds to the distal margin of the abutment 104 and similarly the mesial margin of the temp 115 corresponds to the mesial margin of the abutment 105. With other retraction devices, it would be far more difficult to retract and take an impression of abutment margins which are located more subgingivally as evidenced by the distal abutment margin 104. Once the retraction material is inserted into the internal cavity 114 of the temp 112 and is compressed by the temp along the tooth abutment, the retraction material 170 is expressed precisely beyond (apical to) the abutment margin filling the sulcus 110.

FIG. 9. Illustrates the retraction material 170 filling and compressing the gingival sulcus 110. As more pressure is placed on the top of the temp 112 by having the patient bite on a cotton roll 132, the retraction material 170 compresses further into the sulcus 110 firmly yet gently and atraumatically, and overflows the sulcus 110 therby minimizing excessive and potentially harmful manipulation and trauma of the sulcus 110. The sulcus is left open and dry and unharmed. Retraction is thereby safely, quickly, efficiently, precisely and predictably obtained.

Figure 10:
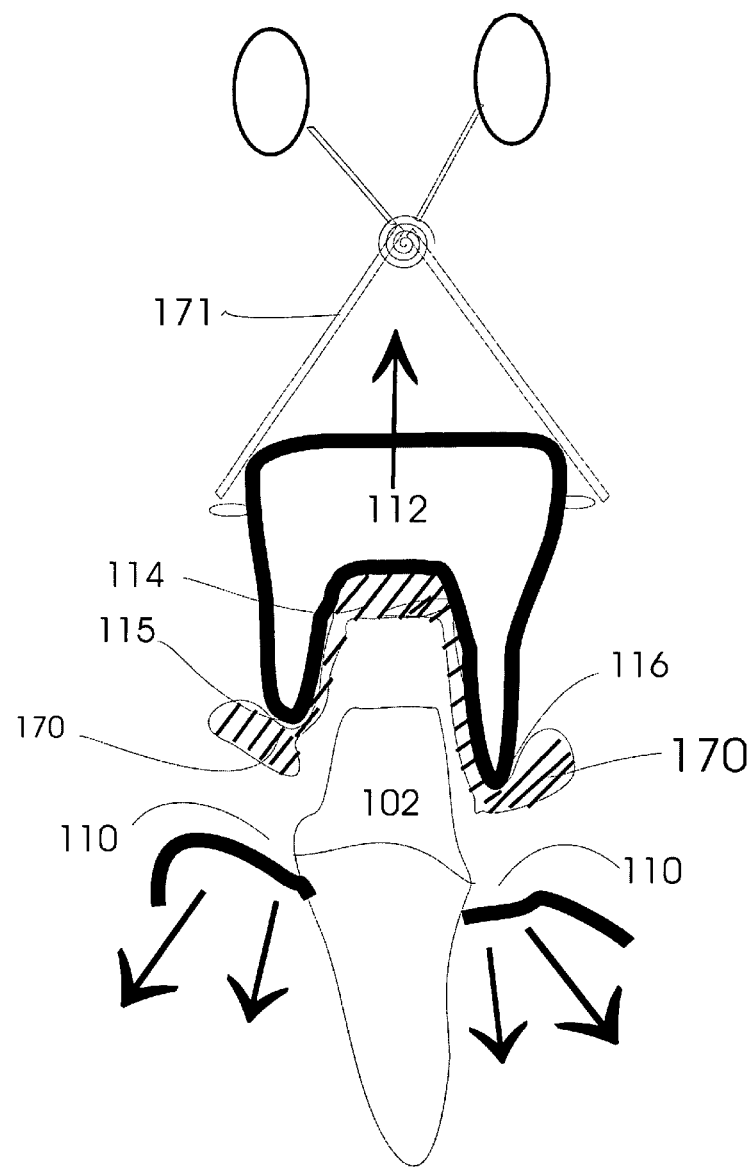
FIG. 10 is a longitudinal cross-sectional view of a human tooth, similar to FIG. 9. demonstrating the atraumatic removal of the retraction material as it is attached to and coincidentally withdrawn with the provisional restoration by dental forceps and producing efficient, complete and precise retraction leaving the sulcus open, dry, and ready to receive impression material.

FIG. 10 demonstrates the atraumatic removal of the retraction material 170 as it is attached to and coincidentally withdrawn with the provisional restoration 112 by dental forceps 171 and producing efficient, complete and precise retraction leaving the sulcus 110 open, dry, and ready to receive impression material. Note that the semi solid, or hardened, or set retraction material does not stick to the gingiva 106 nor the tooth abutment 102 but sticks onto the interior of the "temp" 114 and is therefore removed from the widened sulcus 110 as the "temp" 112 is withdrawn using dental forceps 171.

Figure 11:
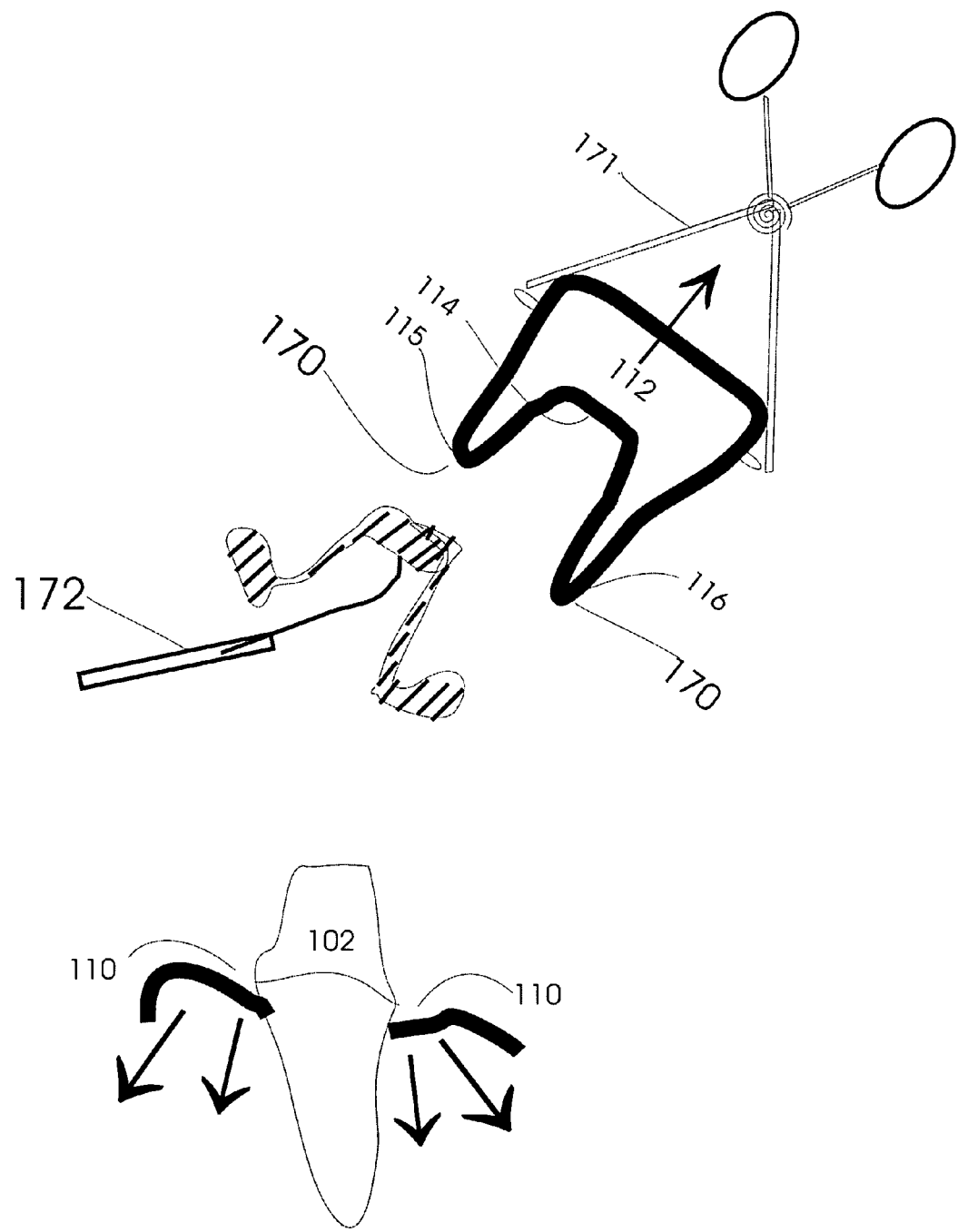
FIG. 11 illustrates the easy removal of the retraction material from the interior cavity of the "temp". This is done after the retraction and impression stages before cementing the "temp" on the prepared tooth abutment (not shown).

FIG. 11 illustrates the easy removal of the retraction material 170 from the interior cavity of the "temp" 114 with a sharp dental instrument 172. This is done after the retraction and impression stages before cementing the "temp" 112 on the prepared tooth abutment (not shown). The "temp" therefore has three functions in addition to providing temporary coverage of an abutment tooth. Firstly it serves as a vehicle to transport the retraction material 170 to the abutment tooth 102; secondly it serves as a template which compresses the retraction material axially and gingivally precisely apical to the abutment margin; thirdly it serves as a vehicle to easily and quickly and atraumatically withdraw the retraction material from the sulcus.

Figure 12:
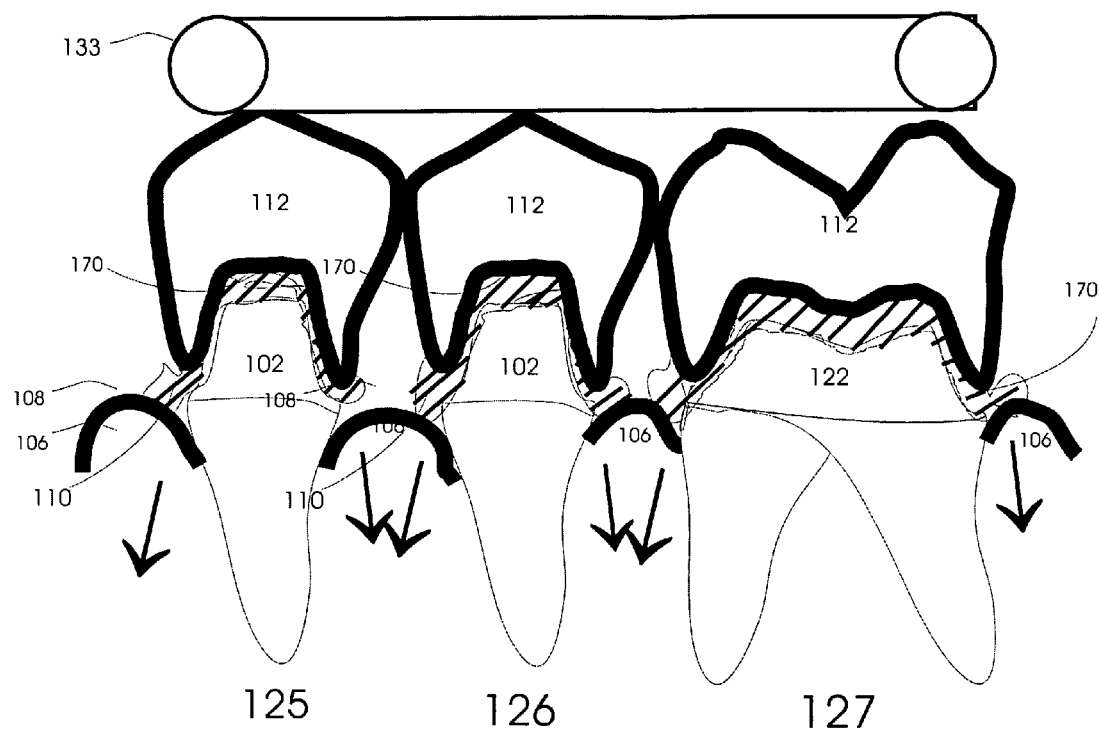
FIG. 12 is a longitudinal cross section view of an embodiment of a device of the present invention suitable for use with a plurality of teeth.
Figure 13:
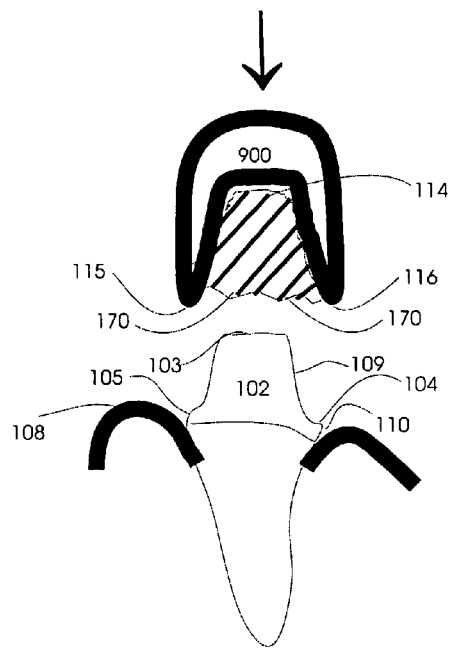
FIGS. 13, 14, 15, 16, Refer to the longitudinal cross section of a pressure cap which acts in a manner similar to the "temp" as it carries the retraction paste to the sulcus and compresses said retraction paste causing displacement and retraction of gingival tissues away from the prepared tooth abutment margin.
Figure 14:
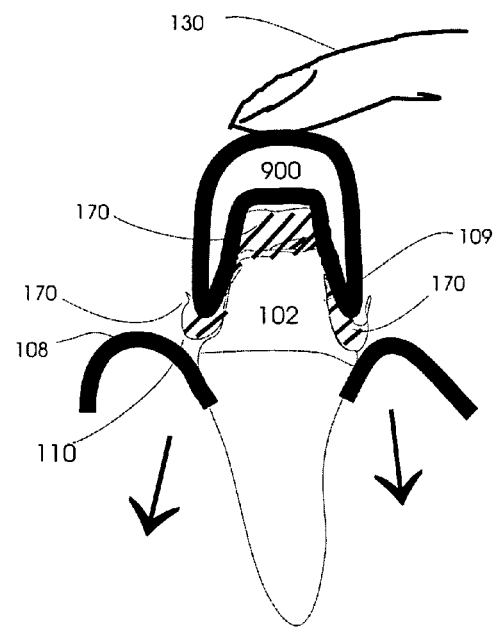
Figure 15:
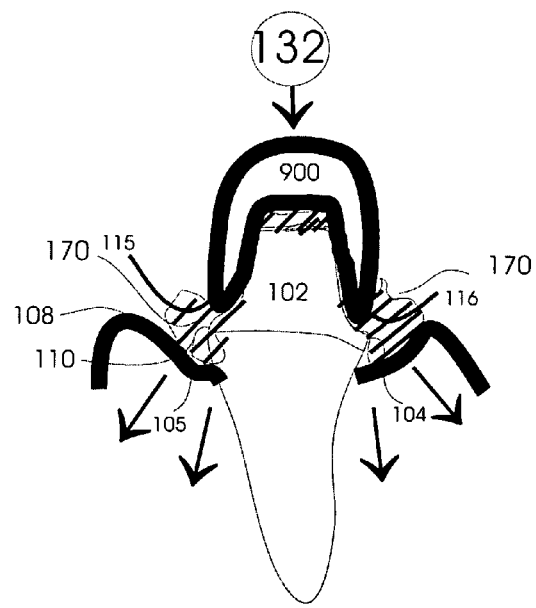
Figure 16:
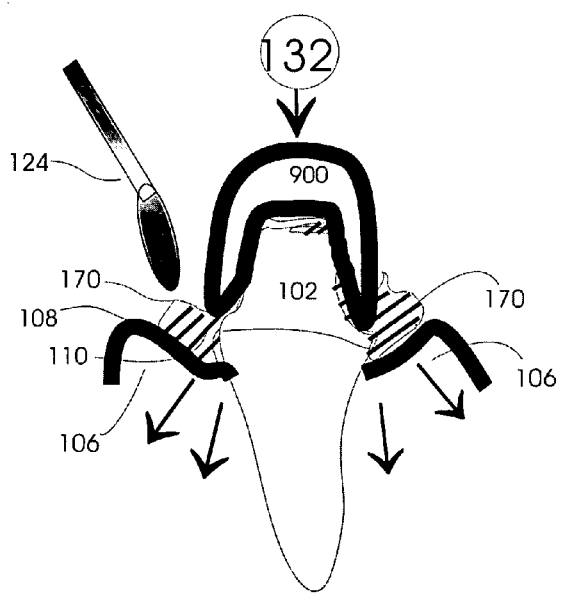

FIG. 12 illustrates a plurality of tooth abutments which can be but are not limited to be individual or joined or splinted together, or can correspond to a bridge (if the middle tooth 126 were absent). This plurality can consist of more than one tooth or less than 16 teeth. Preferably a looser mix or slower set of retraction material 170, to allow for a longer working time to fill a plurality of temps, (more liquid or less powder in the case of liquid powder composition or less catalyst and more base as in the case of polyvinylsiloxane or polyether composition) is placed into the internal aspect of the temp 114 and then seated on the abutments 102 and 104 of teeth 125, 126, and 127. Because the "temp" precisely fits the abutment teeth 102 and 122, as the temp is compressed down having the patient bite down on a cotton roll 133 placed along, the mesial/distal length of the "temp", the retraction material is compressed simultaneously over the plurality of abutments in a manner similar to FIG. 5. FIG. 12 illustrates the embodiment of a device of the present invention suitable for use with a plurality of teeth 125, 126, 127, demonstrating the effective, continuous, retraction of the sulcii of the plurality of teeth on the facial and lingual as well as interproximal aspects. Because interproximal sulci of adjacent teeth are fragile and limited in width, the compression of the soft, smooth retraction material 170 interproximally is more effective, more precise and less traumatic than the other retraction devices currently available.

FIGS. 13, 14, 15, 16, refer to a pressure cap 900 being used in a similar fashion as the "temp." as demonstrated in FIGS. 1 through 12 inclusively.

The above description of preferred embodiments should not be interpreted in a limiting manner since other variations, modifications, and refinements are also possible with the spirit and scope of the present invention. The scope of the invention is defined in the appended claims and their equivalents.

The invention claimed is:

1. A method of preparing a tooth for a dental procedure comprising the steps of:
   (A) removing a portion of the tooth to create a tooth abutment;
   (B) preparing a provisional restoration;
   (C) placing a device for retracting gingival tissue away from the tooth around the tooth abutment;
   (D) placing the provisional restoration on the tooth abutment on top of the device;
   (E) causing pressure to be exerted on the provisional restoration to pack the device into a sulcus associated with the tooth.

2. A method of preparing a tooth for a dental procedure as described in claim 1, further comprising the step of removing the provisional restoration from the tooth abutment and thereby removing the device atraumatically from the sulcus.

3. A method of preparing a tooth for a dental procedure as recited in claim 1, wherein the material consists essentially of one selected from the group consisting of cotton, putty, paste, gel, sponge, jelly, foam, cellulose, silicone, plastic, polyvinylsiloxane, and polyether.

4. A method of preparing a tooth for a dental procedure comprising the steps of:
   (A) removing a portion of the tooth to create a tooth abutment;
   (B) preparing a provisional restoration;
   (C) associating a device for retracting gingival tissue away from the tooth with the provisional restoration;
   (D) placing the provisional restoration on the tooth abutment;
   (E) causing pressure to be exerted on the provisional restoration to cause the device to be packed into a sulcus associated with the tooth.

5. A method of preparing a tooth for a dental procedure as described in claim 4, wherein the provisional restoration has a margin, and the step of associating the device for retracting gingival tissue away from the tooth with the provisional restoration comprises the step of releasably adhering the device to the margin of the provisional restoration.

6. A method of preparing a tooth for a dental procedure as described in claim 4, further comprising the step of removing the provisional restoration from the tooth abutment and thereby removing the device atraumatically from the sulcus.

7. A method of preparing a tooth for a dental procedure as described in claim 4, wherein the provisional restoration has a cavity, and the step of associating the device for retracting gingival tissue away from the tooth with the provisional restoration comprises the step of placing the device within the cavity.

8. A method of preparing a tooth for a dental procedure as described in claim 4, wherein the device is one of a putty, paste and a gel.

9. A method of preparing a tooth for a dental procedure as described in claim 4, further comprising the step of removing the provisional restoration from the tooth abutment and thereby removing the device from the sulcus.

* * * * *